(12) United States Patent
Cabrera et al.

(10) Patent No.: US 7,478,009 B2
(45) Date of Patent: Jan. 13, 2009

(54) APPARATUS AND METHOD FOR EVALUATING A HYPERTONIC CONDITION

(75) Inventors: Michael Normann B. Cabrera, Winston-Salem, NC (US); James A. Norris, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 11/191,489

(22) Filed: Jul. 29, 2005

(65) Prior Publication Data

US 2007/0027631 A1 Feb. 1, 2007

(51) Int. Cl.
 *G01N 33/48* (2006.01)
(52) U.S. Cl. .................. 702/141; 702/150; 702/47; 600/587; 600/595; 600/591; 482/6
(58) Field of Classification Search ................ 702/141, 702/150, 47; 482/6; 600/595, 587, 591
 See application file for complete search history.

(56) References Cited

U.S. PATENT DOCUMENTS

| 5,919,115 | A | * | 7/1999 | Horowitz et al. ............... 482/6 |
| 5,978,972 | A | * | 11/1999 | Stewart et al. ................ 2/422 |
| 6,307,481 | B1 | | 10/2001 | Lehrman et al. |
| 2003/0139782 | A1 | * | 7/2003 | Duncan et al. ................ 607/48 |
| 2005/0033200 | A1 | * | 2/2005 | Soehren et al. ............. 600/595 |
| 2005/0197717 | A1 | * | 9/2005 | Ragnarsdottir et al. ........ 623/24 |
| 2006/0161218 | A1 | * | 7/2006 | Danilov ........................ 607/45 |
| 2007/0179560 | A1 | * | 8/2007 | Tong et al. .................... 607/48 |

OTHER PUBLICATIONS

T.D. Sanger et al., "Classification and Definition of Disorders Causing Hypertonia in Childhood," Pediatrics, vol. 111, No. 1, Jan. 2003, pp. 89-97.
H. Abe, "Applications Expand for Downsized Piezoelectric Vibrating Gyroscopes," AEI, Apr. 2003, pp. 49, 50.
Murata Manufacturing Co., Ltd. Technical Data Sheet, Piezoelectric Vibrating Gyroscopes (Gyrostar®).
Value Medical Supplies Technical Article, "Development of Accelerometer Devices".
C.T. Leonard et al., "Myotonomer Intra- and Interrater Reliabilities," Arch Phys Med Rehabil, vol. 84, Jun. 2003, pp. 928-932.

(Continued)

*Primary Examiner*—Tung S Lau
*Assistant Examiner*—Hien X Vo
(74) *Attorney, Agent, or Firm*—Dann, Dorfman, Herrell and Skillman, P.C.

(57) ABSTRACT

An apparatus and method for evaluating a hypertonic condition in a movable extremity are described. The apparatus includes an accelerometer, a gyroscope, a force sensor and a data communication device for transmitting data signals to a data processor. The method includes moving a limb through a range of motion about an axis of rotation while measuring parameters such as acceleration, velocity, the force on the limb, and the time to move it through the range of motion. The measured parameters are transmitted to a data processor which generates and displays information that characterizes the hypertonic condition for immediate feedback to the examiner or storage in a database for monitoring of the patient's condition. An apparatus and a method for simulating movement of a limb that has a hypertonic condition based on characterizing information from a real limb are also described.

16 Claims, 6 Drawing Sheets

OTHER PUBLICATIONS

P.H. Veltink et al., "Inertial Sensing in a Hand Held Dynamometer," 18th Annual Intl. Conf. on the IEEE Eng. in Med. and Bio. Soc., Amsterdam 1996, pp. 502, 503.

M.E. Roebroeck et al., "Reliability Assessment of Isometric Knee Extension Measurements With a Computer-Assisted Hand-Held Dynamometer," Arch Phys Med Rehabil, vol. 79, Apr. 1998, pp. 442-448.

A.D. Pandyan et al., "Biomechanical examination of a commonly used measure of spasticity," Clinical Biomechanics, 16 (2001), pp. 859-865.

K. Tong et al., "A practical gait analysis system using gyroscopes," Medical Engineering & Physics, 21 (1999), pp. 87-94.

PowerLab screen shot of web page, Goniometer (Join Angle Sensor).

PowerLab screen shot of web page, Tendon Hammer.

PowerLab screen shot of web page, Electromyography (EMG).

J. Harlaar et al., "Computer-assisted hand-held dynamometer: low-cost instrument for muscle function assessment in rehabilitation medicine," Med. & Biol. Eng. & Comput., Sep. 1996, pp. 329-335.

B. Ashworth, "Preliminary Trial of Carisoprodol in Multiple Sclerosis," The Practitioner, Apr. 1964, vol. 192, pp. 540-542.

R. Boyd et al., "Objective measurement of clinical findings in the use of botulinum toxin type A for the management of children with cerebral palsy," Euro. Jour. of Neur. 1999 vol. 6(supp. 4) pp. S23-S35.

M.K. Lebiedowska et al., "Quantitative Evaluation of Reflex and Voluntary Activity in Children With Spasticity," Arch Phys Med Rehabil, vol. 84, Jun. 2003, pp. 828-837.

A.E. Tuzson et al., "Spastic Velocity Threshold Constrains Functional Performance in Cerebral Palsy," Arch Phys Med Rehabil, vol. 84, Sep. 2003, pp. 1363-1368.

Arthur Prochazka's Lab screen shot of web page, Rigidity Analyzer.

M.M. Mirbagheri et al., "Intrinsic and reflex stiffnessin normal and spastic, sinal cord injured subjects," Exp Brain Res (2001) 141:446-459.

R. Boyd et al., "Validity of a clinical measure of spasticity in children with cerebral palsy in a randomized clinical trial," Dev. Med. & Child Neurology, Supplement No. 78, Aug. 1998, vol. 40.

R. Boyd et al., "Medium-Term response characterisation and risk factor analysis of botulinum toxin type A in the management of spasticity in children with cerebral palsy," Euro Jour of Neur 1999, 6(suppl) pp. S37-S45.

L. Andrew Korman et al., "Tardieu and modified Tardieu scales," Botulinum Toxin Type A in the Management of Cerebral Palsy, © 2002.

H-M Lee et al., "Quantitative analysis of the velocity related pathophysiology of spasticity and rigidity in the elbow flexors," J Neurol Neurosurg Psychiatry 2002; 72:621-629.

H-M Lee et al., "Validation of portable muscle tone measurement device for quantifying velocity-dependent properties in elbow spasticity," Jour. of Electromyography and Kinesiology 14 (2004) 577-589.

* cited by examiner

APPARATUS AND METHOD FOR EVALUATING A HYPERTONIC CONDITION

BACKGROUND OF THE INVENTION

Hypertonia is a condition of abnormally increased resistance to externally imposed movement about a joint. It may be caused by or manifested as spasticity, dystonia, rigidity, or a combination of such symptoms. Spasticity is a velocity-dependent resistance of a muscle to stretching. Therefore spasticity can be defined as hypertonia in which one or both of the following signs are present: (1) resistance to movement that increases with increasing speed of stretch and varies with the direction of joint movement, and (2) resistance to movement that rises rapidly above a threshold speed or joint angle. This form of hypertonia is common in patients with neurological conditions such as cerebral palsy, stroke, spinal cord injury, traumatic brain injury, or upper motor lesions. During clinical evaluation, spasticity manifests itself as a "catch" or increased resistance during the application of passive joint range of motion at or above a threshold velocity. The foregoing definitions are explained in greater detail in Sanger, T. D. et al., *Classification and Definition of Disorders Causing Hypertonia in Childhood*, Pediatrics 111:e89-e97 (2003).

Clinical classification systems have been designed in attempts to characterize the spastic reflex. Among the known classification systems are the Ashworth and the Tardieu systems. The Ashworth classification is based on the subjective perception of an examiner of the amount of increased resistance to movement felt during a passive range of motion maneuver of a patient's limb. The Tardieu system sought to be more objective and distinguishes specific angles of the limb joint as references for events during the performance of the passive range of motion maneuver. Thus, it identifies the spastic reflex by the angle at which resistance is first detected (R1) and the maximal extent of the angular range of motion (R2).

The Ashworth and Tardieu classification systems rely on examiner-dependent observations. Therefore, they are prone to subjectivity and variance from examiner to examiner and between examinations performed at different times.

Devices designed to objectively quantify muscle function are known. For example, a computer-assisted hand-held dynamometer (CAHNDY®) was developed to make dynamic measurements of muscle function. That device includes a strain gauge force transducer and an electrogoniometer. The former measures the amount of resistance applied to the limb and the latter measures the angle of rotation of the limb about an axis, typically a joint. The signals from the force transducer and the electrogoniometer are transmitted to a computer where they are processed to provide graphs of net moment on the limb as a function of the angle of displacement.

The MYOTONOMETER® device is a handheld electronic device that is designed to measure data for quantifying muscle stiffness. It does this by making a noninvasive assessment of muscle tone when the muscle is at rest and during contraction of the muscle. The probe measures muscle displacement under various conditions of applied force.

The BIODEX system is a manually operated therapeutic and diagnostic apparatus with an output monitor. It is usually used as an isokinetic machine to measure knee function and for knee rehabilitation. It has been used to measure the stretch reflex changes after intrathecal baclofen dosage adjustments in cerebral palsy patients.

Although the foregoing devices and systems provide useful information on muscle function and condition to the clinician, their utility in reliably and effectively quantifying hypertonia and presenting data characterizing such conditions is limited. More specifically, the known devices and systems and devices leave something to be desired with respect to the processing of the raw data and with respect to the presentation of the data in user-friendly graphical and absolute value formats. Accordingly, it would be desirable to have a device or system that is capable of reliably measuring indicia of hypertonia. It would also be desired that such a device can be used in a standardized examination protocol to provide real-time quantitative measurements of relevant parameters that are objective and reproducible.

SUMMARY OF THE INVENTION

The disadvantages of the known devices and methods are overcome to a significant degree by the devices and associated methods according to the present invention.

In accordance with a first aspect of the present invention, there is provided an apparatus for evaluating a hypertonic condition such as spasticity in an extremity. The apparatus includes an accelerometer, a gyroscope, and a pressure sensor. A base is provided in the apparatus on which the accelerometer, gyroscope, and the pressure sensor are mounted. The apparatus further includes a data communication device adapted for transmitting data signals from said accelerometer, said gyroscope, and said pressure sensor. The data transmitted from the apparatus can be processed locally during therapy or rehabilitation sessions to provide the examiner or the patient with real-time feedback about the patient's condition.

In accordance with a second aspect of the present invention there is provided a method of evaluating a hypertonic condition such as spastic reflex of an extremity. The method includes the step of moving the extremity through a range of motion about an axis of rotation. During the movement of the limb the acceleration of a point on the extremity, the angular velocity at which the extremity moves in the range of motion, the force applied to the extremity as it is moved through the range of motion, and the time duration to move the extremity through the range of motion are all measured in real time. The measured acceleration, angular rate, force, and time, are then transmitted to a data processor which processes the data to generate information that characterizes the hypertonic condition of the extremity. As an additional feature of the method according to this aspect of the invention, the characterizing information and data are stored in a database for later retrieval and use.

In accordance with another aspect of the present invention there is provided a method for monitoring a hypertonic condition of a patient. The method according to this aspect of the invention includes the step of first identifying an extremity of the patient which has a hypertonic condition. The method continues with the step of moving the extremity through a range of motion about an axis of rotation. During the movement of the extremity the acceleration of a point on the extremity, the angular velocity at which the extremity moves in the range of motion, the force applied to the extremity as it is moved through the range of motion, and the time duration to move the extremity through the range of motion are all measured. The measured acceleration, angular rate, force, and time, are then transmitted to a data processor which processes the data to generate information that characterizes the hypertonic condition of the extremity. The characterizing information is preferably stored in a database of such information. The information can be retrieved from the database and compared to previously obtained characterizing information for the hypertonic condition in the patient so that any change in the condition as a result of treatment or therapy and changes in the characteristics of the evaluation or maneuvering of the limb can be readily determined.

In accordance with a further aspect of the present invention there is provided an apparatus for simulating movement of a limb that has a hypertonic condition. The apparatus according to this aspect includes an electric motor adapted to be driven by a control voltage. An artificial limb is attached to the electric motor so as to be rotated by it. A control processor is operatively connected to the electric motor for providing the control voltage thereto. The control processor is programmed with parameters of position, velocity, and torque that represent the motion of a real limb having a hypertonic condition, whereby the control voltage is varied by said control processor. The parameters for programming the simulator are preferably obtained from a database of such information as described above relative to other aspects of this invention.

In accordance with a still further aspect of this invention, there is provided a method of simulating a hypertonic condition in a limb to aid in the training of examiners. This method includes the step of programming a control processor with desired parameters of position, velocity, and torque that characterize the hypertonic condition during motion of the limb. The control processor generates a control voltage based on the desired parameters. The control voltage is applied to an electric motor that drives an artificial limb, whereby the artificial limb is rotated in a manner that simulates the movement of a real limb. The parameters for programming the simulator are preferably obtained from a database of such information as described above relative to other aspects of this invention.

BRIEF DESCRIPTION OF THE DRAWINGS

The foregoing summary as well as the following detailed description will be better understood when read in connection with the drawings wherein.

DETAILED DESCRIPTION

Figure 1:
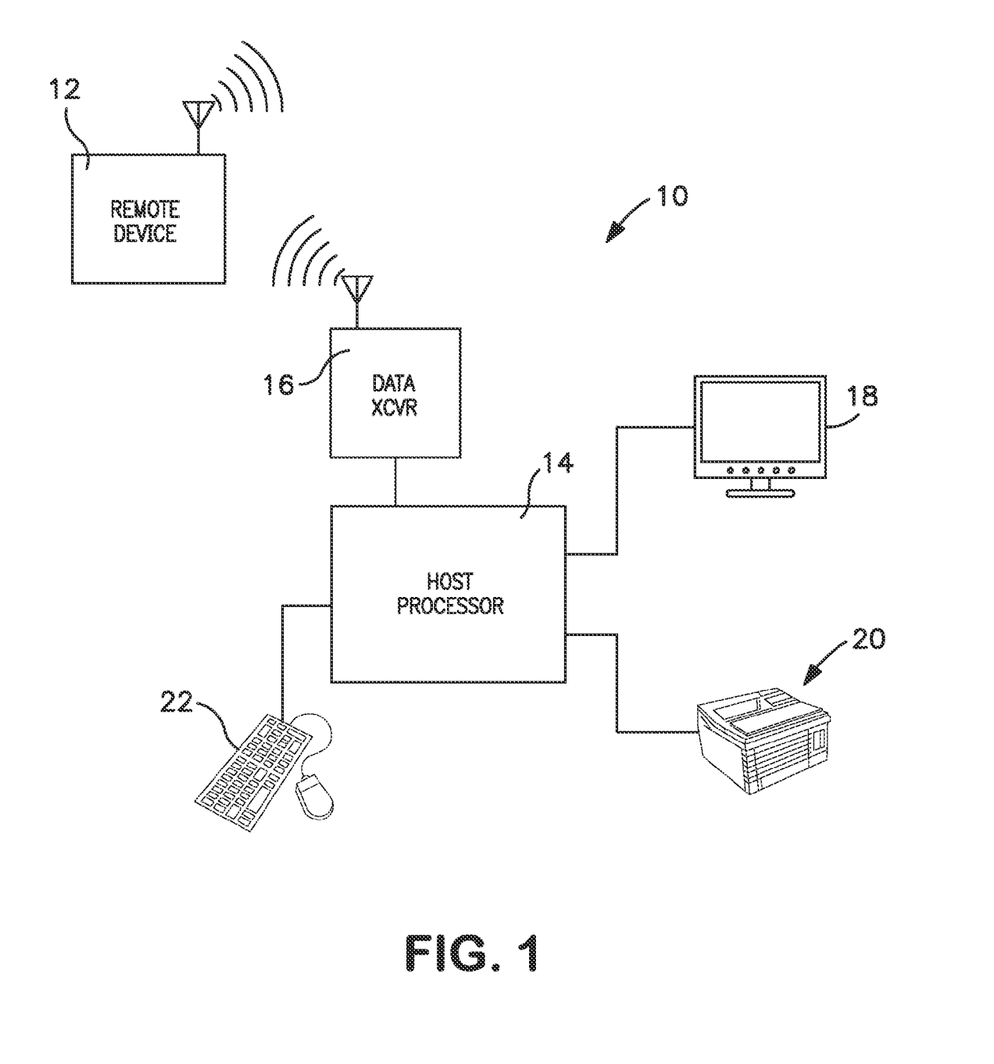
FIG. 1 is a schematic block diagram of a system in accordance with the present invention.

Referring now to the drawings, and in particular to FIG. 1, there is shown a system 10 for quantifying and evaluating hypertonia in a human subject. The system 10 includes a remote device 12 and a host processor 14 having a data transceiver 16. Various peripheral devices such as a display monitor 18, a printer 20, and a keyboard and mouse 22 are operably connected to the host processor 14 to permit data input and output operations. For example, information such as subject identification, date and time, and requests for data output displays can be manually input using the keyboard and mouse 22. The input information as well as graphs and data charts of measured parameters can be displayed on the monitor 18 and printed on the printer 20.

Figure 2:
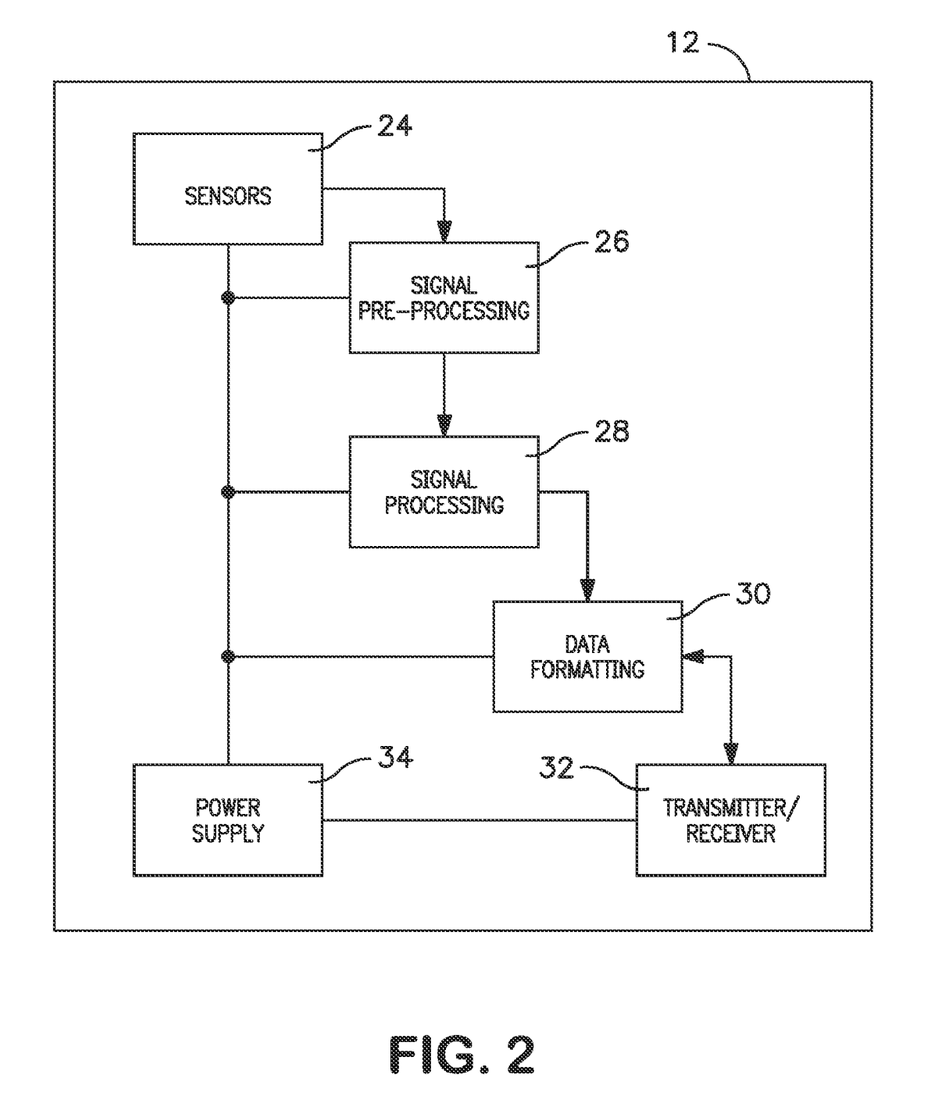
FIG. 2 is a schematic block diagram of a remote device used in the system shown in FIG. 1.

The remote device 12 is preferably embodied as a self-contained package that can be used remotely from the host processor 14. It is preferably small and lightweight so that it can be applied to a limb of the subject to be examined. It is preferably configured for wireless transmission and reception of data signals, but could be hard-wired to the host processor if desired. As shown in FIG. 2, the remote device 10 includes sensors 24. Preferably, the sensors include an accelerometer, a gyroscope, and a force or pressure sensor. The sensors provide data signals that relate to parameters such as position and displacement of the subject's limb and the force applied to move it through a range of motion. The remote device 12 also includes data processing means connected to the sensors 24 for processing data signals generated by the sensors. Toward that end a signal preprocessor 26 is connected to receive data signals from the sensors 24. The signal preprocessor 26 includes circuits and electronic devices for amplifying the signals, filtering extraneous information from the data signals, and/or smoothing the received signals. A further signal processor 28 is connected to receive the pre-processed data signals from the signal preprocessor 26. The signal processor 28 includes logic circuits for mathematically deriving other information from the basic data signals. For example, the signal processor 28 would be configured to keep track of orientation of the remote device 12 in space, detect certain types of events based on the data received, and limit the amount of data that actually needs to be transmitted to the host processor 14 to provide an accurate representation of the motion of the limb being examined.

Once the data signals have been processed, they must be formatted for transmission to the host processor 14. A data formatting circuit 30 is included in the remote device 12 for that purpose. The data formatting circuit 30 includes analog-to-digital converters, buffer memory, and data encoders. A wireless transceiver 32 is connected to receive the encoded data signals from the data formatting circuit 30. The transceiver 32 is configured for transmitting the data signals to the host processor 14 using standard wireless protocols. The wireless transceiver also includes a receiver section to receive command signals transmitted from the host processor 14. Such signals include commands for turning the remote device 12 on or off, commands to reset the remote device memory registers, and other utilitarian functions. An onboard power supply 34 is included in the remote device 12 to provide electric power to the various sensors and devices. The power supply 34 includes a battery and voltage regulation circuits as needed to provided a stable source of power to the sensors 24, the signal processing circuits 26 and 28, the data formatting circuit 30, and the wireless transceiver 32.

Figure 5:
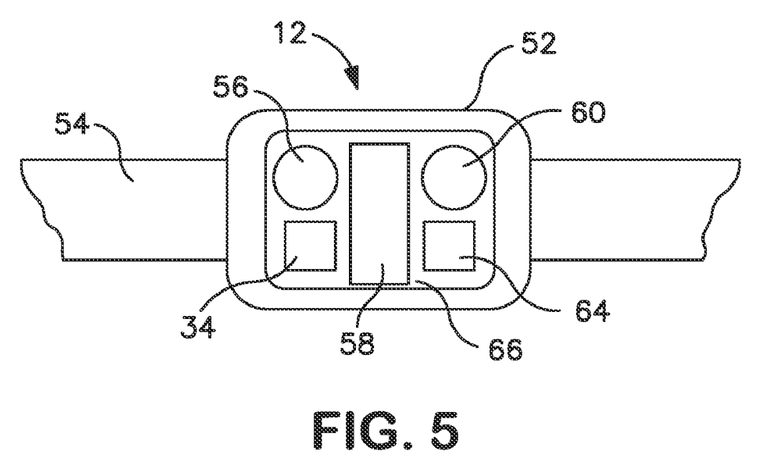
FIG. 5 is a partial top plan view of an embodiment of the remote device shown in FIG. 2.

Shown in FIG. 5 is a preferred arrangement of the remote device 12. The remote device 12 has a case 52 for encapsulating the sensors and the other electronic circuits and devices used in the remote device. A strap 54 is coupled to the case 52 so that the remote device 12 can be attached to the limb of a patient. An accelerometer 56, a gyroscope 58, and a pressure transducer 60 are mounted and connected on a circuit board 66. The accelerometer 56 can be realized by any of the known miniature accelerometer devices such as those made and sold by Analog Devices under Model No. ADXL202. The gyroscope 58 can be realized by any of the known miniature gyroscope devices such as those made and sold by Murata Manufacturing Co. under the name "GYROSTAR". The pressure transducer can be realized by any known miniature pressure transducer such as the Model MPX10 made by Motorola Inc. Also mounted and connected on the circuit board 66 are the power supply 34 and the electronic circuit devices 64 for processing and transmitting the data signals to the host processor 14.

Figure 3:
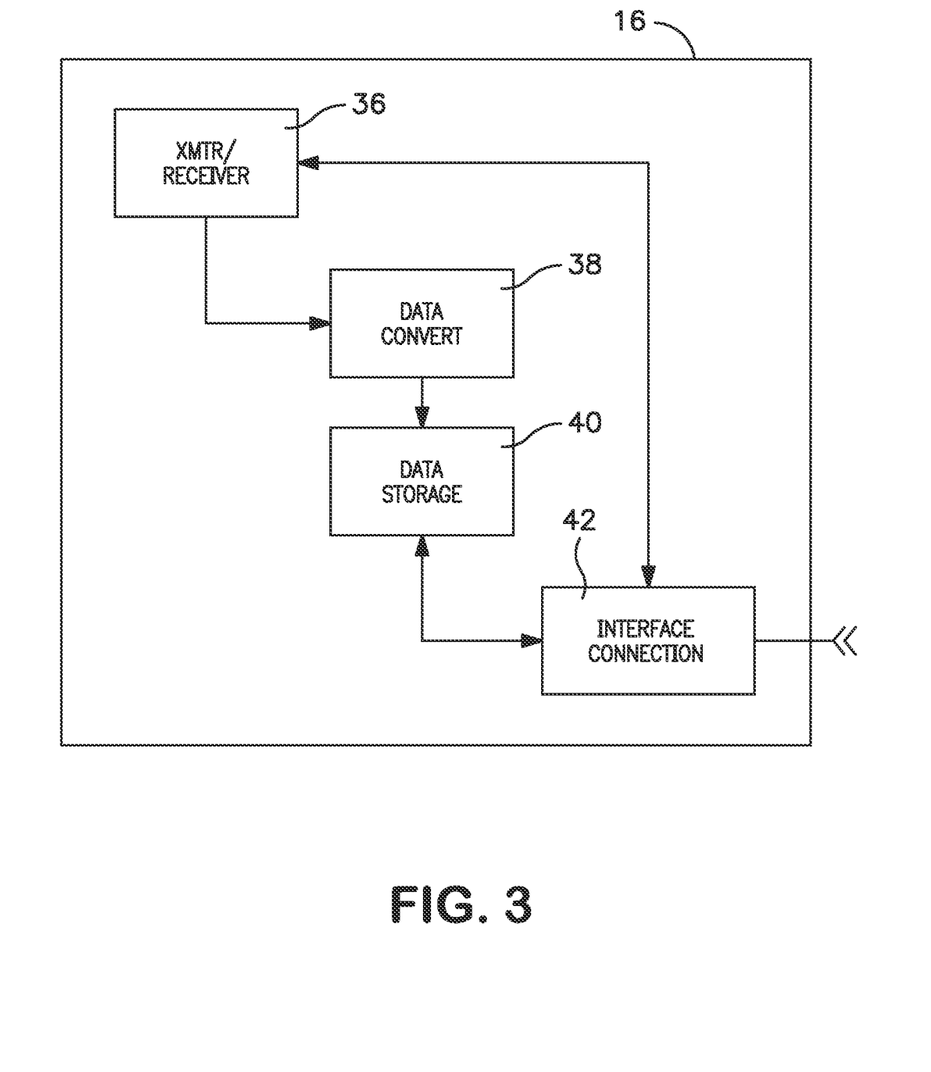
FIG. 3 is a schematic block diagram of a data transceiver used in the system shown in FIG. 1.

Referring now to FIG. 3, there is shown a preferred arrangement for the data transceiver 16 used in the system according to the present invention. The data transceiver 16 includes a wireless transmitter/receiver section 36 which is configured similarly to the wireless transceiver 32 on the remote device 12. The data transceiver 16 may be embodied as a wireless pc adapter of the types which are widely available. The wireless transmitter/receiver section 36 receives data signals transmitted from the remote device 12. The data signals would include not only data signals from the sensors, but also utility information such as battery level and error codes produced by any of the onboard circuits. A data conversion circuit 38 is connected to receive the data signals from the transmitter/receiver 36. It is configured to decode the data signals and re-format them for communication to the host processor 14. A data storage circuit 40 is connected to receive the re-formatted data signals from the data conversion circuit 38. The data storage circuit 40 includes data storage devices such as random access memory modules for buffering the data signals to the host processor 14. A standard interface connection 42 is connected to receive the data signals from the data storage circuit 40 for input to the host processor. The interface connection 42 can be embodied as a PCI adapter, USB connection, or other standard-type data communication interface. Although the primary function of the data transceiver 16 is the reception and handling of data signals from the remote device 12, it is contemplated that it will also be operable to transmit data signals to the remote device. In this regard, it would function to transmit commands from the host processor to the remote device for effecting certain operations in the remote device. Such operations would include turning the remote device on or off, clearing memory registers, etc., as described above.

Figure 4:
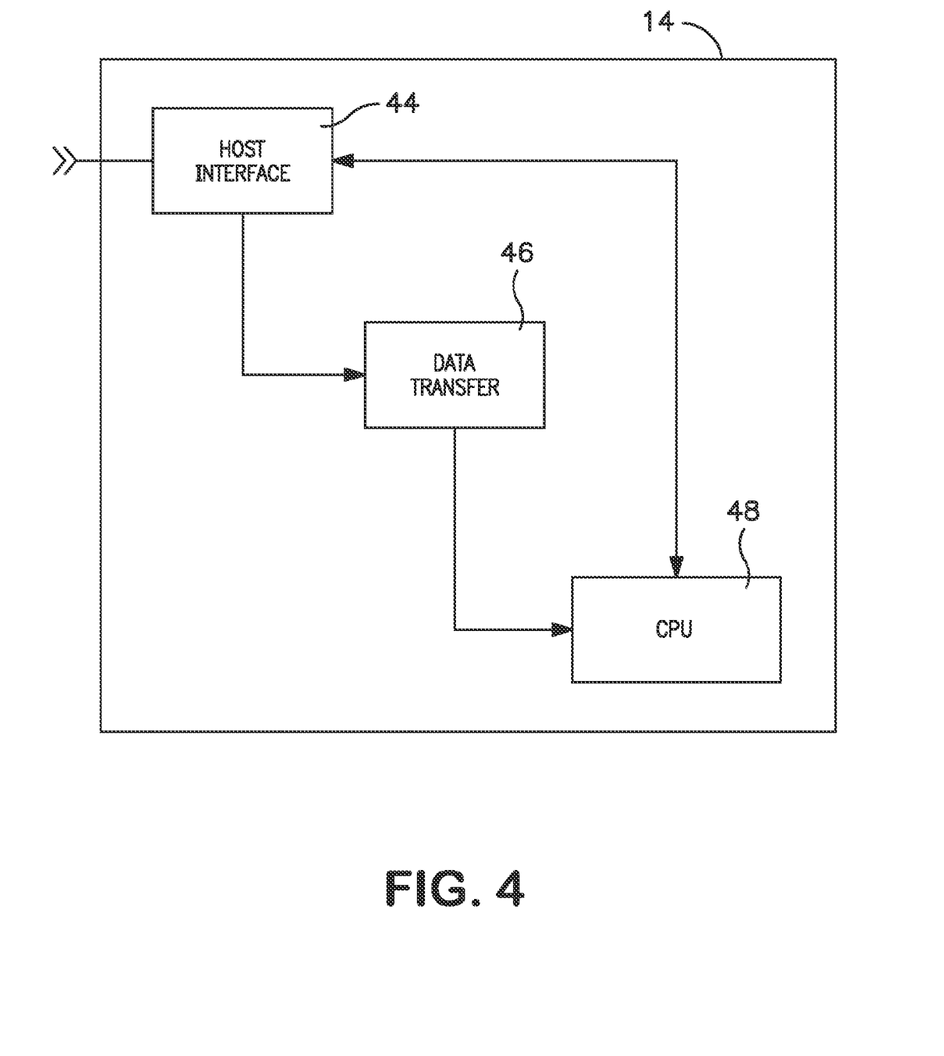
FIG. 4 is a schematic block diagram of a host processor used in the system shown in FIG. 1.

Referring to FIG. 4, there is shown a preferred arrangement for the host processor 14 used in the system according to the present invention. The host processor 14 may be realized as a stand-alone type personal computer such as a desktop or notebook computer. It is also contemplated that the host processor 14 could be embodied as a portable hand-held device such as a PDA, palm pc, or a special purpose device. The host processor 14 includes a hardware interface 44 for connection with the data transceiver 16. A data transfer circuit 46 is connected to receive the data signals from the interface 44. The data transfer circuit 46 includes data storage and handling devices to facilitate transfer of the incoming data to a permanent storage device, such as a hard disk drive, and to the central processing unit 48.

The central processing unit 48 can be any of the known personal computer-type CPU's such those manufactured and sold by Intel Corporation, Advanced Micro Devices, or Apple Computer Inc. When the host processor 14 is embodied as a hand-held device, the central processing unit would be a CPU for any of the known hand-held devices such as those manufactured and sold by PALM Inc., Hewlett-Packard Inc., or Dell Computer Inc. The central processing unit 48 runs the software used to manipulate the data received from the remote device 12 to provide usettl information to the therapist or physician. The central processing unit 48 runs software that performs additional filtering of the data to remove unwanted or unneeded signal components. The software would also be configured to integrate or differentiate the angular velocity and acceleration data signals from the remote device to calculate an absolute position in space, to calculate a joint angle or angles as a function of time, or to quantify aspects of the received data that are relevant to the motion of the limb or joint kinematics, such as the joint angle and velocity when a spastic catch occurs. In addition, the software would permit the graphic representation of desired parameters as a function of another parameter to graphically illustrate aspects of motion during a spastic catch or other condition.

The host processor 14 is programmed to determine several parameters that can be used to quantify a spastic reflex, including, the angular and linear velocity of a point on the patient's limb, the angular and linear acceleration of that point, the absolute position and the change in position of that point over time, the location and the change in location of the point over time, and the torque or amount of resistance present when the limb is moved through its range of motion.

The quantities measured and calculated by the system 10 according to the present invention can be used to standardize the description and characterization of a spastic reflex throughout its range of motion. The data can also be displayed in real time to provide virtually instantaneous feedback to the clinician or the therapist. The raw data generated by the remote device can also be processed to yield a set of identifying characteristics or parameters that would aid in diagnosing a disease state.

It is a further feature of the system according to this invention that the host processor will run software that provides the ability to store the received data in a database. The database would be organized similar to the known medical patient databases and provide for rapid searching of computerized patient records. The data stored in the database could be used to track the effect on a hypertonia condition over time or over a series of therapeutic treatments for the condition. Additionally, the information in the database would permit a therapist or medical practitioner to quickly recall and compare response data for multiple patients who have similar symptoms of hypertonia or have some other user-specified common criteria. For example, it would be possible to quickly extract data for all patients that exhibited a specific type of response as quantified by the sensors in the remote device 12. The capability to quickly review multiple patients provides a means to assess outcomes of a group of patients who may be subjected to different treatments. The information obtained by such an analysis would greatly assist in deciding which treatment or treatments are most effective for a particular type of patient. It is further contemplated that the data in the database can be used to generate parameters for programming a simulator as described more fully hereinbelow.

Further, the data and graphical representations of the measured parameters provided by the system of this invention will standardize the evaluation of hypertonic spasticity resulting from a neurological condition. Such standardization is similar to an electrocardiogram (ECG) that is documented, reproducible, and understood by physicians around the world. The standardization of the evaluation of the spastic reflex in patients will have a significant impact on the treatment and management of neurological conditions. For example, an evaluation of such a condition performed prior to the patient receiving medical treatment can be objectively compared to an evaluation done after such treatment. Such comparisons are difficult, if not impossible, to perform using the current techniques because the known assessment technique relies primarily on the skill and experience of the therapist or clinician performing the procedure.

Use of the system described above to quantify and represent a spastic reflex or other hypertonia will now be described in connection with various methods. Examination for evaluating hypertonia, and more particularly, a spastic reflex, in an extremity involves moving a segment of the extremity through a passive range of motion at a preselected velocity. A proximal segment of the extremity is held stationary in order to serve as a reference for determining the resistance to movement of the moving segment and the angle formed between the moving segment and the proximal segment. By convention, the angle at the position of rest or at the maximum extension of the movable segment is defined as zero (0) degrees. It will be appreciated that the system described herein can also be used with active range of motion by the patient himself/herself when desired.

Figure 6:
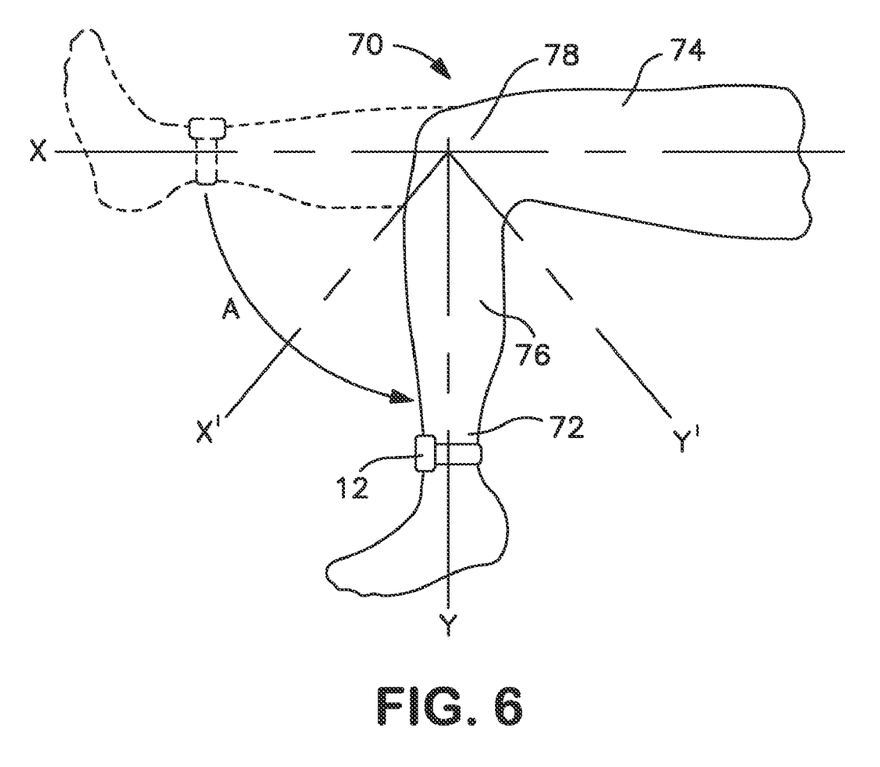
FIG. 6 is a schematic view of a human leg showing the use of the remote device of FIG. 5.

In geometric terms, the extremity to be tested has at least two segments at least one of which is movable relative to the other segment(s). The movable segment has a specified axis of rotation that is defined to be perpendicular to the plane of motion. A point on the movable segment is selected at a known distance from the axis of rotation. That point will move through an arc as the movable segment is moved through the range of motion. As shown in FIG. 6, a leg 70 has a thigh segment 74 and a movable segment 76. An axis of rotation is defined through the knee 78 and would be perpendicular to the plane of the paper. The movable segment 76 can be rotated about that axis. A point is defined at the ankle 72 of the leg 70. The remote device 12, described above, is attached or applied to the movable segment 76 at or adjacent to the ankle 72. The ankle 72 will have a defined acceleration as the movable segment 76 is moved through a range of motion, for example, between points X and Y, or between points X' and Y'. The acceleration is sensed by the accelerometer in the remote device 12. The gyroscope in the remote device 12 senses the initial location of the ankle 72 and its change in position as the movable segment 76 is moved through the range of motion. The pressure transducer in the remote device 12 senses the force applied to the leg segment 76 as it is moved through the range of motion. Although the data accumulation portion of the method according to the present invention has been described with reference to examination relating to movement about the knee joint, it is contemplated that data can also be acquired using the remote device 12 for examinations relating to movements about the hip, the ankle, the elbow, and any other extremity that rotates about an axis through a joint.

It is also a feature of this aspect of the present invention that more than one remote device can be used during an examination. For example, in evaluating a hypertonic condition in an arm, a remote device can be attached or placed on the upper portion of the arm, i.e., above the elbow, and a second remote device can be applied to the forearm. Such an arrangement would allow evaluation of more complex movements about multiple joints. The use of multiple remote devices for collecting data is facilitated by the use of wireless communication of the data from the remote units to the central processor. Moreover, the remote device can be constructed with multi-axis sensors or multiple sensors for measuring the acceleration, angular velocity, and force in two or three dimensions and about two or three axes.

In a preferred format of the examination process, a musculoskeletal evaluation of the spastic condition using the Ashworth and Tardieu systems will be performed by the examiner or therapist with the remote device 12 in place. The examinations will be performed in multiple sets. Each set of examinations, evaluating the patient's involved and noninvolved extremities, will consist of passive range of motion maneuvers performed at various examiner-selected speeds. The actual speeds are selected to elicit a spastic reflex in the extremity that can be sensed with the remote device and evaluated.

The values of the measured parameters, acceleration, angular velocity, distance, and force, are transmitted to the host processor. The host processor performs mathematical operations with the parameter values to obtain additional parameters such as angular displacement and angular velocity. The various parameters are then displayed, either in real time or delayed, in graphical forms to provide useful information about the spastic reflex of the patient being tested. Such graphical representations may include acceleration as a function of time, angular displacement as a function of time, and angular velocity as a function of angular displacement. The graphical data representations are not limited to the listed examples because others could be readily defined by the clinician or physician for specific purposes or special hypertonic conditions. The graphical or other data representations can be stored in a database for the patient, as described above, for later retrieval as a basis of comparison, for example, after therapeutic treatment or against other patients with similar conditions.

Figure 7:
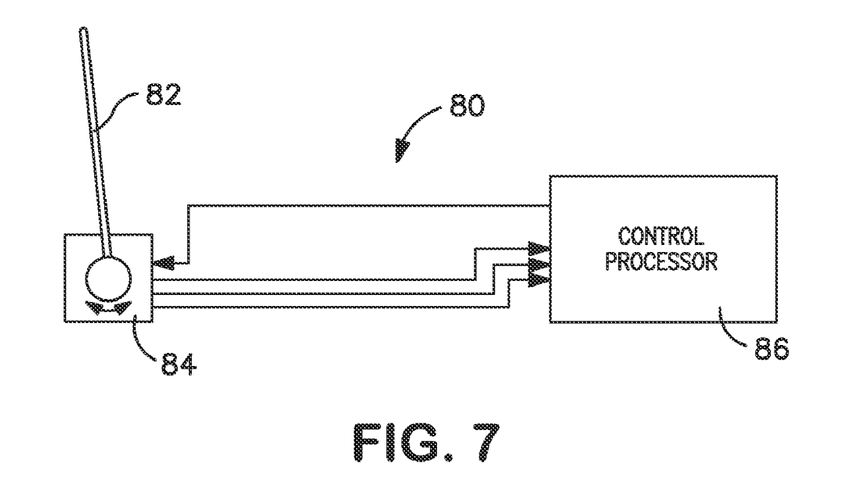
FIG. 7 is a schematic block diagram of a device for simulating a subject having a hypertonia condition.

Referring now to FIG. 7, there is shown a simulator device 80 in accordance with another aspect of the present invention. The simulator device 80 is adapted to simulate the motion of an extremity of a patient having a hypertonic condition that results from a neurological disorder. The simulator device 80 includes an artificial limb 82 that is coupled to a motor 84. The artificial limb 82 is constructed to be similar to a real limb, such as an arm or leg, in terms of weight and moment of inertia. The artificial limb 82 is coupled to the motor 84 in such a manner that when it is moved by the motor, the motion is similar to that of the limb being simulated. A control processor 86 is connected to the motor 84. The control processor 86 is programmed to provide control signals, preferably a control voltage ($V_c$) to the motor 84 to drive the motor in a manner that simulates the movement of a limb. The control processor 86 is programmed to generate control signals that drive the motor 84 to provide a limb motion that is normal or one that manifests a hypertonic reflex. The control processor 86 would include either a logic circuit or a CPU that executes a software code to generate the desired control signals.

Figure 8:
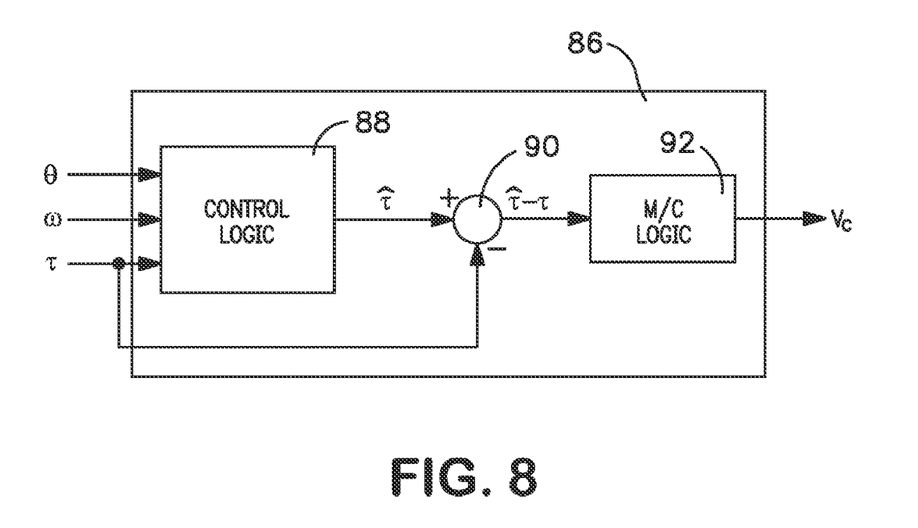
FIG. 8 is a schematic diagram of the control processor used in the simulator device shown in FIG. 7.

Shown in FIG. 8 is a preferred arrangement of the control processor 86. The control processor 86 utilizes a feedback loop based on angular position ($\theta$), angular velocity ($\omega$), and torque ($\tau$) parameters from the artificial limb 82 and motor 84. Signals representing those parameters are input to the control processor 86. All of the parameters are input to an empirical control logic 88. The empirical control logic 88 is programmed to calculate a desired torque signal ($\tau_D$). The actual torque signal and the computed torque signal are summed at a summing amplifier 90 to provide an error signal ($\tau_D$-$\tau$). The error signal is input to the motor control logic circuit 92 and is used to compute an updated control voltage ($V_c$). The empirical control logic 88 is programmed to provide the relationships between the position, velocity, and torque parameters for different spastic responses. The computational relationships are based on the results of testing patients using the system described above. The computational logic can also be derived from published data and feedback from physicians who work with patients having a spastic condition.

A system and method have been described for use in connection with the quantitative evaluation of a hypertonic condition in a patient. The system provides a wide scope of utility in connection with the assessment and treatment of patients having such conditions. The system and method are useful in the evaluation of hypertonic conditions associated with, but not limited to the following: cerebral palsy, traumatic brain injury, cerebrovascular disease such as childhood stroke, chronic spinal cord injury, hereditary spastic paraparesis, and neurodegenerative disorders such as metachromatic leukodystrophy, Pelizaeus Merzbacher disease, neuronal ceroid lipofuscinosis, and Hallervorden-Spatz syndrome. The system according to this invention can be used to characterize a hypertonic condition exhibited during a range of motion examination in terms of velocity, joint angle displacement, muscular resistance, chronology of events, and duration of events.

The system and method of this invention can be used to standardize clinical measurement and evaluation of results and to standardize the procedure of testing in order to produce reliable, reproducible results for long term patient follow-up or patient-to-patient comparison.

The system and method described herein may be used to monitor a patient's response to medical and/or surgical treatment of spasticity. Likewise, measurements made using the disclosed system can be used to characterize the natural history of the disease process.

The system according to this invention device can facilitate documentation of a spastic reflex or other hypertonic condition in the form of easily understandable graphs and tables. Such documentation also will facilitate communication and exchange of information between health providers and may be used to help physicians differentiate between disease conditions. Further, the data in the form of graphs and tables may be archived in a database for future comparison and for research purposes.

The system and method according to the present invention are useful not only for passive testing, but also for evaluating active, voluntary motion of patients. In this regard, the system can be used to give positive real time feedback to patients undergoing therapy and treatment (e.g., muscle stretching and strengthening). Moreover, the system and method can be used in connection with other techniques for assessing muscular activity such as electromyography. In this regard, it is contemplated that the remote device could incorporate a probe for electromyography.

Further, the data acquired with the apparatus and system of this invention may be used to program and control the operation of a device for simulating the motion of a limb manifesting a hypertonic condition. Such simulation can be utilized for educational, research, and training purposes.

It will be recognized by those skilled in the art that changes or modifications may be made to the above-described embodiments without departing from the broad inventive concepts of the invention. It is understood, therefore, that the invention is not limited to the particular embodiments which are described, but is intended to cover all modifications and changes within the scope and spirit of the invention as described in the appended claims.

What is claimed is:

1. Apparatus for evaluating spasticity in a movable extremity of a patient comprising:
    an accelerometer for measuring the acceleration of a point on the extremity during movement thereof in a range of motion of the extremity;
    a gyroscope for measuring the angular velocity at which the extremity moves in the range of motion;
    a sensor adapted for measuring the force applied to the extremity as the extremity is moved through the range of motion;
    a data communication device adapted for transmitting data signals from said accelerometer, said gyroscope, and said sensor;
    a base on which said data communication device, said accelerometer, said gyroscope, and said sensor are mounted;
    means for attaching said base to the extremity;
    a data processor mounted on said base and connected between said accelerometer, said gyroscope, said sensor, and said data communication device for processing the data signals to modify a characteristic of the data signals prior to their being transmitted by said data communication device, said the data processor comprising
        a first processor adapted for receiving the data signals from said accelerometer, said gyroscope, and said sensor and for performing a first pre-processing operation on said data signals to provide first pre-processed data signals; and
        a second processor adapted for receiving the first pre-processed data signals and for performing a second pre-processing operation on said first pre-processed data signals to provide second pre-processed data signals.

2. A device as set forth in claim 1 further comprising data formatting means for formatting the second pre-processed data signals to be transmitted by said data communication device.

3. A device as set forth in claim 1 further comprising an electric power source operatively connected to said accelerometer, said gyroscope, said sensor, and said data communication device for providing electric power to said accelerometer, said gyroscope, said sensor, and said data communication device.

4. A method of evaluating a hypertonic condition of an extremity, comprising the steps of:
    moving the extremity through a range of motion about an axis of rotation;
    measuring the acceleration of a point on the extremity during the movement thereof;
    measuring the angular velocity at which the extremity moves in the range of motion;
    measuring the force applied to the extremity as the extremity is moved through the range of motion;
    measuring the time duration to move the extremity through the range of motion;
    processing the measured acceleration, angular velocity, force, and time, to generate information that characterizes the hypertonic condition of the extremity; and then
    displaying the characterizing information to obtain a visually perceptible representation of the response of the extremity as the extremity traverses the range of motion.

5. A method as set forth in claim 4 wherein the following steps are performed after the measuring steps:
    generating an acceleration signal corresponding to the measured acceleration;
    generating an angular velocity signal corresponding to the measured angular velocity;
    generating a force signal corresponding to the measured force; and
    transmitting the acceleration signal, the angle signal, and the force signal to a data processor wherein said processing step is performed.

6. A method as set forth in claim 4 further comprising the step of recording the characterizing information in a manner adapted for subsequent retrieval.

7. A method as set forth in claim 4 wherein the processing step comprises the step of calculating data characterizing the joint kinematics of the extremity when moved through the range of motion.

8. A method as set forth in claim 4 wherein the processing step comprises the step of generating a set of identifying characteristics of the hypertonic condition that would aid in the diagnosing of a disease state.

9. A method of monitoring a hypertonic condition of a patient comprising the steps of:
- identifying an extremity of the patient which has a hypertonic condition;
- moving the extremity through a range of motion about an axis of rotation;
- measuring the acceleration of a point on the extremity during the movement thereof;
- measuring the angular velocity at which the extremity moves in the range of motion;
- measuring the force applied to the extremity as the extremity is moved through the range of motion;
- measuring the time duration to move the extremity through the range of motion;
- transmitting the acceleration, the angular velocity, and the force to a data processor;
- processing the measured acceleration, angle, force, and time, to generate information that characterizes the hypertonic condition of the extremity;
- comparing the characterizing information to previously obtained characterizing information for the hypertonic condition of the patient; and then
- determining whether a change in the hypertonic condition has occurred.

10. A method as set forth in claim 9 wherein the step of processing the measured acceleration, angular velocity, force, and time comprises the step of storing the characterizing information in a computer database.

11. A method as set forth in claim 9 wherein the step of comparing the characterizing information comprises the step of retrieving previously stored characterizing information from the computer database.

12. A method as set forth in claim 9 wherein the step of processing the measured acceleration, angular velocity, force, and time comprises the step of displaying the characterizing information to provide a visually perceptible representation of the hypertonic condition of the extremity.

13. A method as set forth in claim 9 wherein the step of processing the measured acceleration, angular velocity, force, and time comprises the step of storing a visually perceptible representation of the hypertonic condition of the extremity in a computer database.

14. An apparatus for simulating movement of a limb that has a hypertonic condition comprising:
- an actuator adapted to be driven by a control signal;
- an artificial limb attached to said actuator so as to be rotated by said actuator;
- a control processor operatively connected to said actuator for providing the control signal thereto, wherein said control processor is programmed with parameters of position, velocity, and torque that represent the motion of a real limb having a hypertonic condition, whereby the control signal is varied by said control processor; and
- a feedback loop connected between said actuator and said control processor for providing feedback signals representative of the position, velocity, and torque of the artificial limb to the control processor, whereby an error signal is generated by said control processor for modifying the control signal.

15. An apparatus as set forth in claim 14 wherein the control processor comprises an empirical logic circuit connected to receive the feedback signals and programmed with desired position, velocity, and torque parameters, said empirical logic circuit being operable to provide a desired torque signal based on a comparison of the desired position, velocity, and torque parameters to the feedback signals.

16. A method of simulating a hypertonic condition in a limb comprising the steps of:
- programming a control processor with desired parameters of position, velocity, and torque that characterize the hypertonic condition during motion of a real limb;
- generating a control signal based on said desired parameters; and
- applying the control signal to an actuator that drives an artificial limb;
- wherein the step of programming the control processor comprises the steps of:
- moving a real limb having a hypertonic condition through a range of motion about an axis of rotation;
- measuring the acceleration of a point on the real limb during the movement thereof;
- measuring the angular velocity at which the real limb moves in the range of motion;
- measuring the force applied to the real limb as the real limb is moved through the range of motion;
- measuring the time duration to move the real limb through the range of motion; and then
- processing the measured acceleration, angular velocity, force, and time, to generate information that characterizes the hypertonic condition of the real limb; and then
- programming the control processor with the characterizing information obtained from the real limb.

* * * * *